United States Patent
Mattsson et al.

(10) Patent No.: US 6,326,476 B1
(45) Date of Patent: Dec. 4, 2001

(54) HEPARIN DERIVATIVES AND PROCESS FOR THE PREPARATION THEREOF

(75) Inventors: Christer Jan Mattsson, Sundbyberg; Carl Magnus Erik Svahn, Sollentuna; Michael Per Weber, Kista, all of (SE)

(73) Assignee: Pharmacia AB, Stockholm (SE)

( * ) Notice: Subject to any disclaimer, the term of this patent is extended or adjusted under 35 U.S.C. 154(b) by 0 days.

(21) Appl. No.: 08/438,933

(22) Filed: May 10, 1995

Related U.S. Application Data

(63) Continuation of application No. 07/949,551, filed as application No. PCT/SE92/00243 on Apr. 14, 1992, now Pat. No. 6,150,342.

(30) Foreign Application Priority Data

Apr. 18, 1991 (SE) .................................................. 9101155

(51) Int. Cl.[7] .......................... C08B 37/10; A61K 31/715
(52) U.S. Cl. .............................. 536/21; 536/553; 514/56
(58) Field of Search ........................ 536/21, 55.3; 514/56

(56) References Cited

U.S. PATENT DOCUMENTS

| | | | | |
|---|---|---|---|---|
| 4,727,063 | * | 2/1988 | Naggi et al. ............................ | 514/56 |
| 4,948,881 | * | 8/1990 | Naggi et al. ............................ | 526/20 |
| 4,966,894 | * | 10/1990 | Herr et al. .............................. | 514/56 |
| 5,013,724 | * | 5/1991 | Petitou et al. ......................... | 514/54 |
| 5,164,378 | * | 11/1992 | Conti et al. ............................ | 514/56 |

OTHER PUBLICATIONS

The Merck Index, twelfth edition. Susan Budavari et al., editors. Merck & Co., Inc., Whitehouse, NJ. 1996. Monograph4685, p. 795.*

Fransson *Carbohydr. Res.*1978 , 62, 235–244.*

Fransson et al. *FEBS Lett.*1979, 97(1), 119–123.*

Fransson et al. *Carbohydr. Res.*1980, 80, 131–145.*

Fransson et al. *Eur. J. Biochem.*1980, 106, 56–69.*

Casu et al. *Arzneim.–Forsch./Drug Res.*1986, 36(4), 637–642.*

* cited by examiner

*Primary Examiner*—Kathleen Kahler Fonda
(74) *Attorney, Agent, or Firm*—Connolly Bove Lodge & Hutz

(57) ABSTRACT

The invention relates to new heparin derivatives from bovine or porcine heparin which have a molecular weight equal to or larger than the standard heparin, show a sulfur content which is equal to or higher than that of the starting heparin or at least 13% w/w, have an anticoagulant activity in the anti-FXa assay of less than 10% of the standard heparin it was made from, show a ratio of APTT activity over anti-FXa activity of 3–35, show a reduced prolongation of bleeding time compared to the standard heparin it was made from as measured in the rat tail after i.v. administration and show enhancement of the rate of development of coronary collaterals in dogs equal to or better than clinically used heparin. The invention also relates to processes for preparation of the new bovine and porcine heparin derivatives. The use of this product for the manufacturing of a medicament for treatment of ischemic heart disease and related vascular disorders and for the enhancement of the rate of development of coronary collateral perfusion is disclosed.

6 Claims, 6 Drawing Sheets

HEPARIN DERIVATIVES AND PROCESS FOR THE PREPARATION THEREOF

Figure 1:
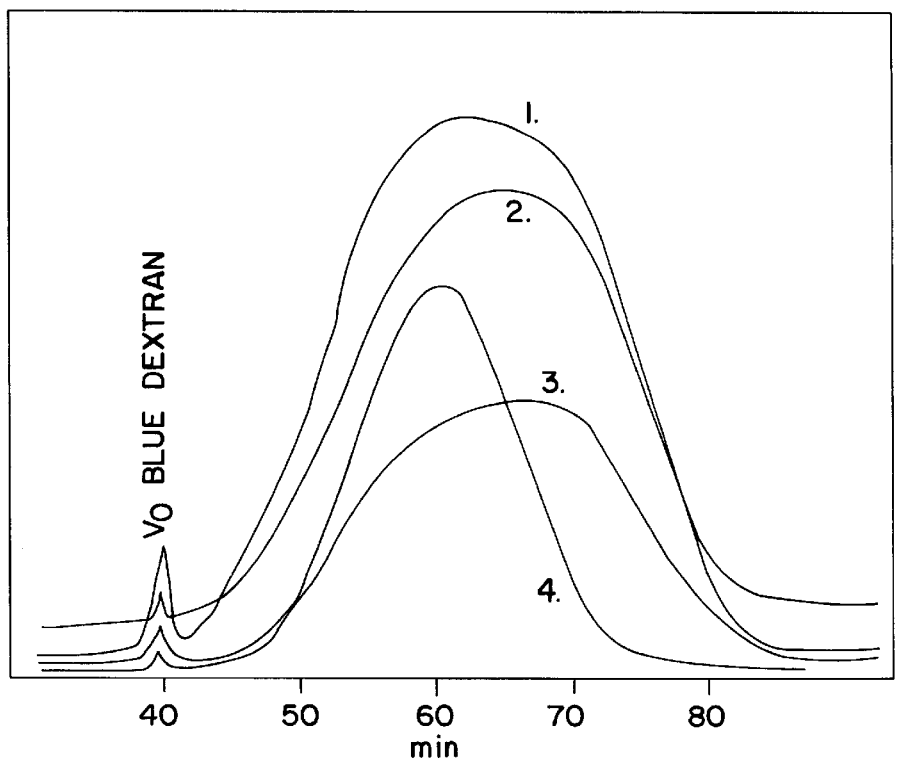

This is a continuation of U.S. Ser. No. 07/949,551, filed Nov. 19, 1992, now U.S. Pat. No. 6,150,342, which is the U.S. national stage entry under 35 U.S.C. §371 of PCT/SE92/00243, filed Apr. 14, 1992.

The present invention relates to novel heparin derivatives for treatment of ischemic heart disease and related vascular disorders and process for the preparation thereof.

BACKGROUND

Heparin is sulfate-containing polysaccharide which on a large scale is isolated from intestinal mucus from swine or lung from cattle. The avarage molecular weight for standard bovine heparin is more than 9,000 and for standard porcine heparin more than 12,000. Traditionally the clinical use of heparin has been associated with its anticoagulant and antithrombotic properties (Jorpes. E. 1946, Heparin in Treatment of Thrombosis, 2nd Ed. Oxford Medical Publications). Heparin has also been found to accelerate coronary collateral development in dogs (Fujita, M. Mikuniya, A. Takahashi, M. Gaddis, R. Hartley, J. McKnown, D. and Franklin, D. 1987, Japanese Circulation Journal, 51, 395–402) and to improve collateral circulation in patients with effort angina (Fujita, M. Sasayama, S. Asanoi, H. Nakijama, H. Sakai, O. and Ohino, A. 1988, Circulation, 77, 1022–1029). Other effects such as the "anti-complementary power of heparin" recognized by Ecker, E. E. and Gross, P. (1929) in J. Infect. Dis. 44, 250–253 and the finding by Clowes, A. W. and Karnovsky, M. J. (1977) in Nature 265, 625–626 that heparin infusion following experimental injury suppressed the proliferation of smooth muscle cells, have not led to any widespread use of heparin for the treatment of diseases related to inflammation or to arteriosclerosis, which are associated with complement activation and smooth muscle cell proliferation respectively. The risk of haemorrhage is considered to be the main limitation for the clinical use of heparin in non-antithrombotic indications.

The patent application EP 287 477-A discloses heparin products with low molecular weight and this document gives a good review of prior art relating to oxidation of heparin by periodate and to low molecular weight heparins obtained in this manner. Reference is herein given to this document.

In EP 287 477, it was shown that, when heparin obtained from porcine intestinal mucosa was subjected to treatment with periodate at pH 5 followed by depolymerization by treatment with a strong base at a pH above 11 and then reduced by a reducing agent, a low molecular weight heparin was obtained which had 70% of its molecular weight distributed between 4800–9000 Da and a peak molecular weight of 5500–6000 Da as determined by HPLC. This low molecular heparin is used for regulation of the physiological system.

We have now found that the low molecular weight heparins (heparin fragments) corresponding to EP 287 477 did not significantly accelerate the coronary collateral development. However, unexpectedly. we have found that our novel heparin derivatives of a molecular weight equal to or larger than standard heparin which have an enhanced sulfur content, retain the valuable physiological properties of standard heparin such as the enhancement of coronary collateral development. In addition we have also shown a much smaller effect on the bleeding time for our novel heparin derivatives than for heparin itself. We have also shown a potent antithrombotic activity of our novel heparin derivatives at a dose in which the bleeding time is not prolonged. Thus our novel heparin derivatives are superior to the products claimed in EP 287 477 and will constitute useful drugs for treatment of ischemic heart disease such as angina and related vascular disorders, e.g. to prevent restenosis after percutaneous transluminal angioplasty (PTCA).

Patients suffering from ischemic heart disease generally show a narrowing of the arteries in the heart. Progressive narrowing of the lumen of coronary arteries gives rise to the symptoms of angina and finally often to a myocardial infarction (MI). Excessive uncontrolled growth of smooth muscle cells (SMC) constitutes a major contribution to the progressive narrowing of the coronary vessel. The final occlusion of a stenotic vessel, which precipitates the myocardial infarction, is most frequently caused by formation of a thrombus. The thrombus formation might be triggered by activation of the coagulation and complement systems which by themselves become activated by the sclerotic surface of the stenotic artery. As a natural defense mechanism to the reduced blood flow and thus reduced oxygen supply to these parts of the heart which are supplied by the stenotic blood vessels new routes of blood supply slowly develop in some patients, whereas in other patients hardly at all. These new routes of blood supply to an oxygen deficient (ischemic) area of the heart are called collaterals and the process of formation of new blood vessels is called angiogenesis. The new routes can be small or large vessels. Here they are collectively referred to as collaterals. It has been shown that heparin has a stimulatory effect on coronary collateral development and the process of angiogenesis as well as an inhibitory effect on SMC proliferation and a preventive effect on thrombus formation. However a major obstacle for a general use of heparin in ischemic heart disease is the risk for bleeding which is associated with therapy using standard heparin. The present invention describes novel heparin derivatives which enhance coronary collateral formation, inhibit SMC proliferation and maintain a low level of anticoagulant activity in blood without being hazardous with respect to bleeding thus being suitable for treatment in ischemic heart disease e.g. angina pectoris and related vascular disorders. An example of related vascular disorders is treatment of patients having had a percutaneous transluminal coronary angioplasty (PTCA) procedure to prevent restenosis.

FIGURE LEGENDS

FIG. 1: Gel permeation chromatography by HPLC

1 Heparin from bovine lung

2 Heparin from bovine lung after periodate oxidation

3 Heparin from bovine lung after periodate oxidation, depolymerization by sodium hydroxide and reduction by sodium borohydride 4 Heparin from bovine lung after periodate oxidation, depolymerization by sodium hydroxide, reduction by sodium borohydride and fractionation (Heparin derivative 1).

Figure 2:
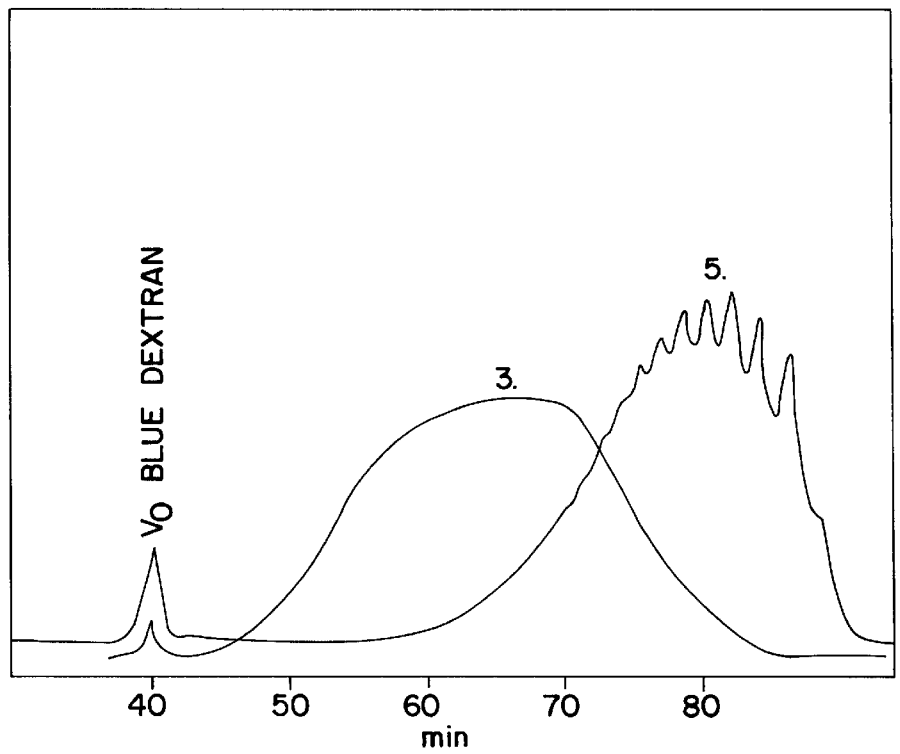

FIG. 2 Gel permeation chromatography by HPLC

Figure 3:
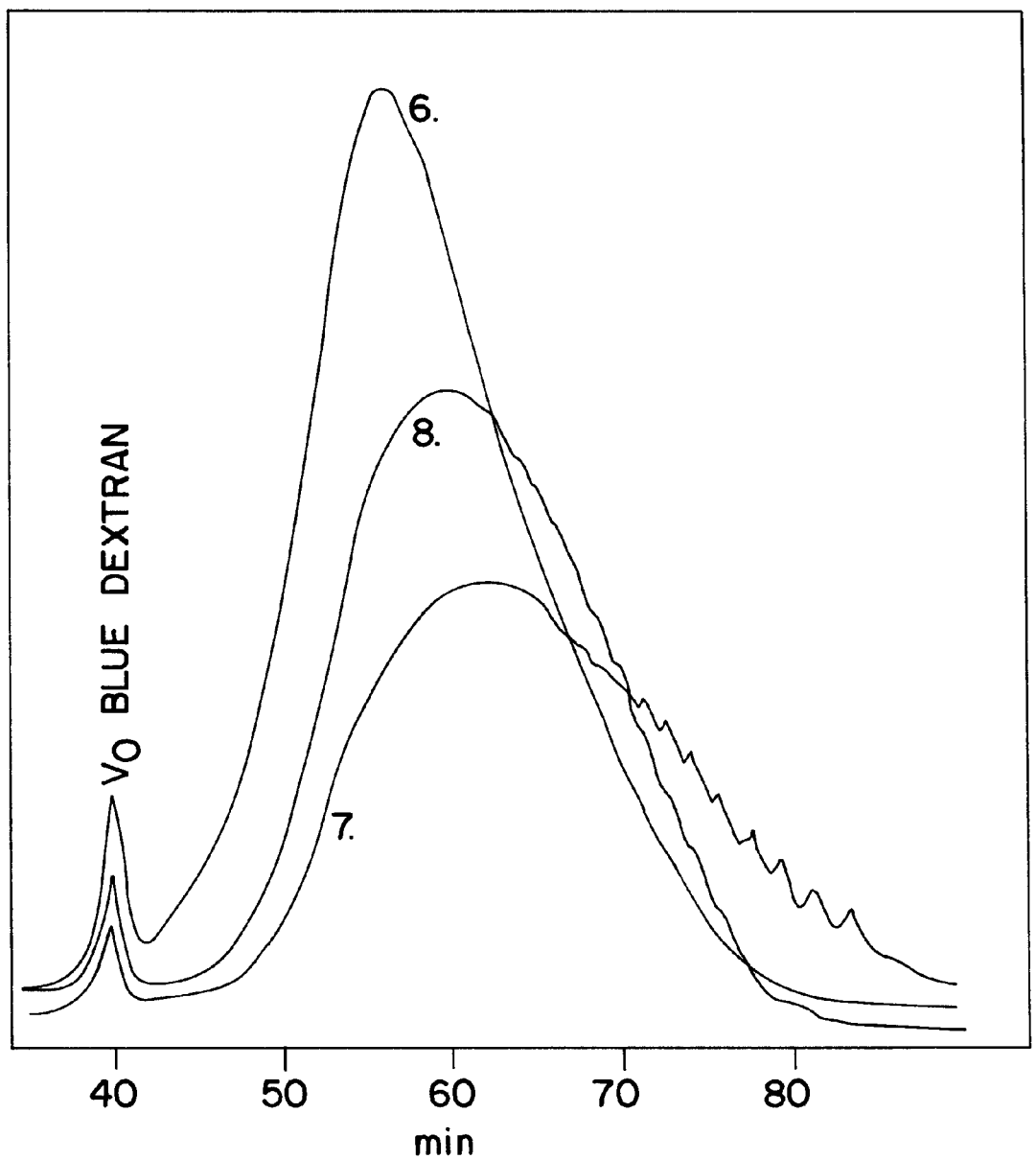

3 Heparin from bovine lung after periodate oxidation, depolymerization by sodium hydroxide and reduction by sodium borohydride 5 Heparin from porcine intestinal mucosa after periodate oxidation, depolymerization by sodium hydroxide and reduction by sodium borohydride FIG. 3 Gel permeation chromatography by HPLC 6 Standard heparin from porcine intestinal mucosa 7 Standard heparin from porcine intestinal mucosa after sulfation, periodate oxidation, depolymerization by sodium hydroxide and reduction by sodium borohydride 8 Standard heparin from porcine intestinal mucosa after sulfation, periodate oxidation, depolymerization by sodium hydroxide and reduction by sodium borohydride and fractionation (Example 5)

Figure 4:
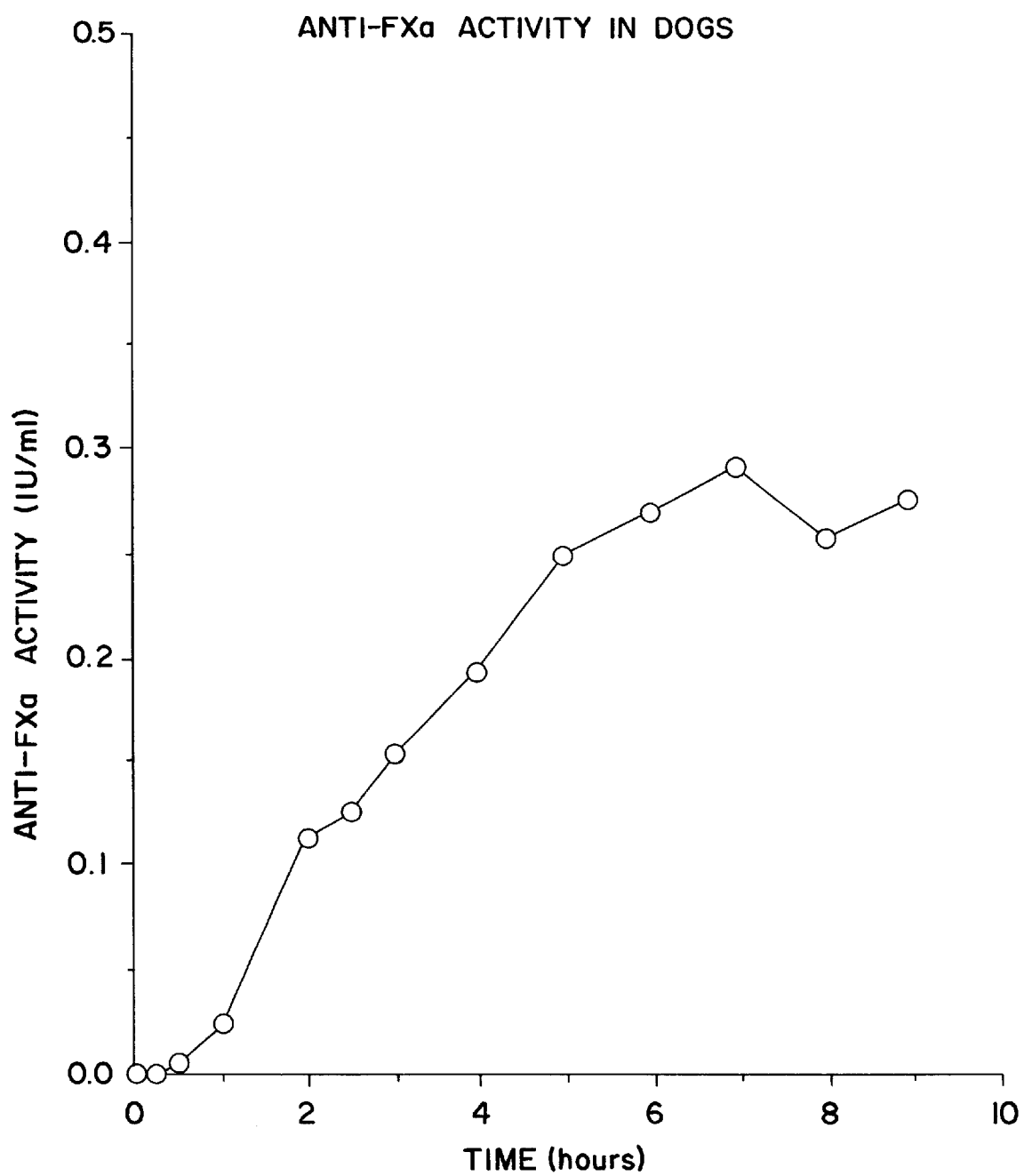

FIG. 4 Anti-FXa activity in dogs after subcutaneous administration of heparin derivative 1 (10 mg/kg). The anti-FXa activity was determined according to Bergkvist et. al. (1983). Thromb. Res. 32 381–391.

Figure 5:
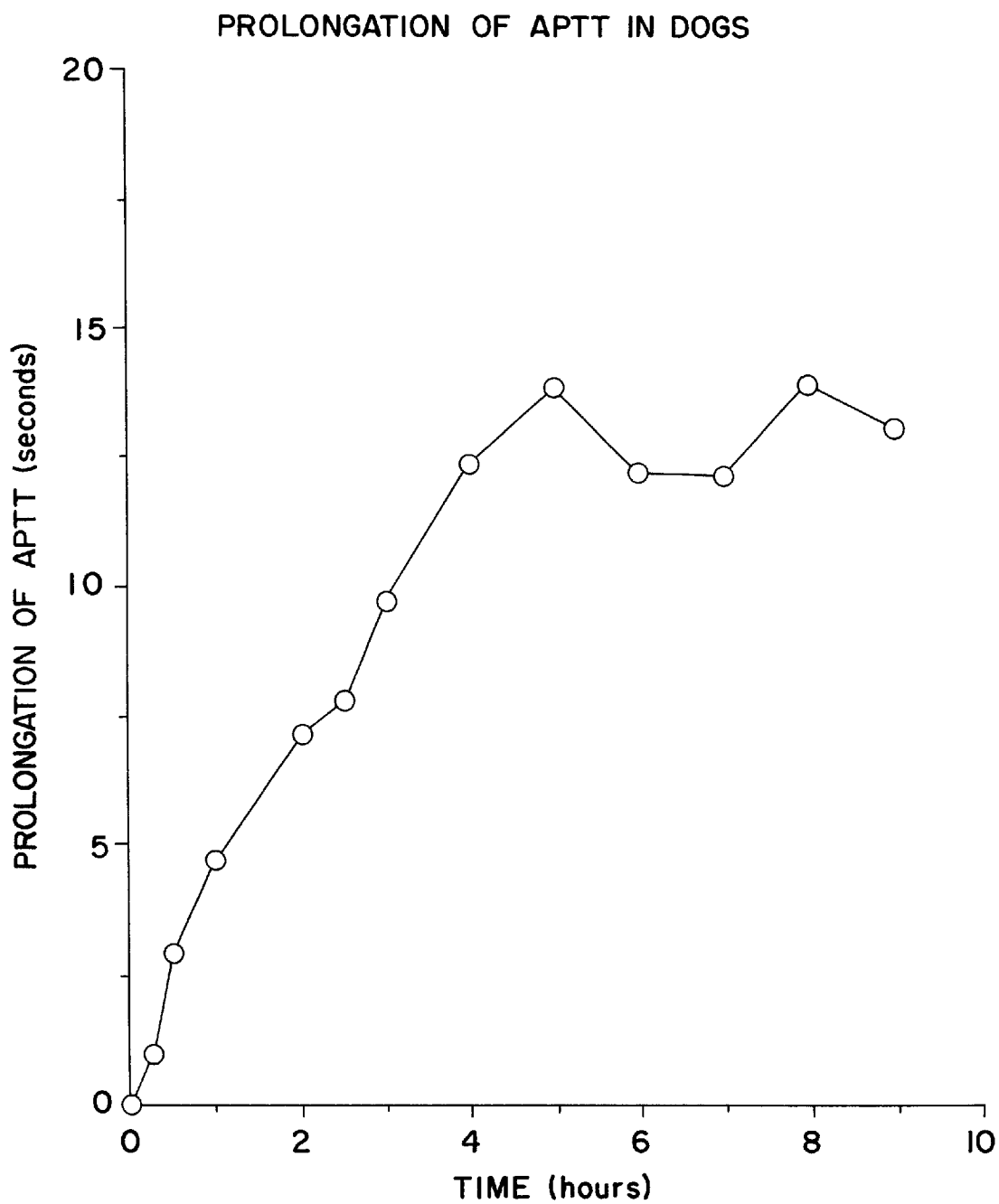

FIG. 5 APTT activity in dogs after subcutaneous administration of heparin derivative 1 (10 mg/kg). The APTT activity was determined according to Teien el. al. (1975). Thromb. Res. 7 777–778.

Figure 6:
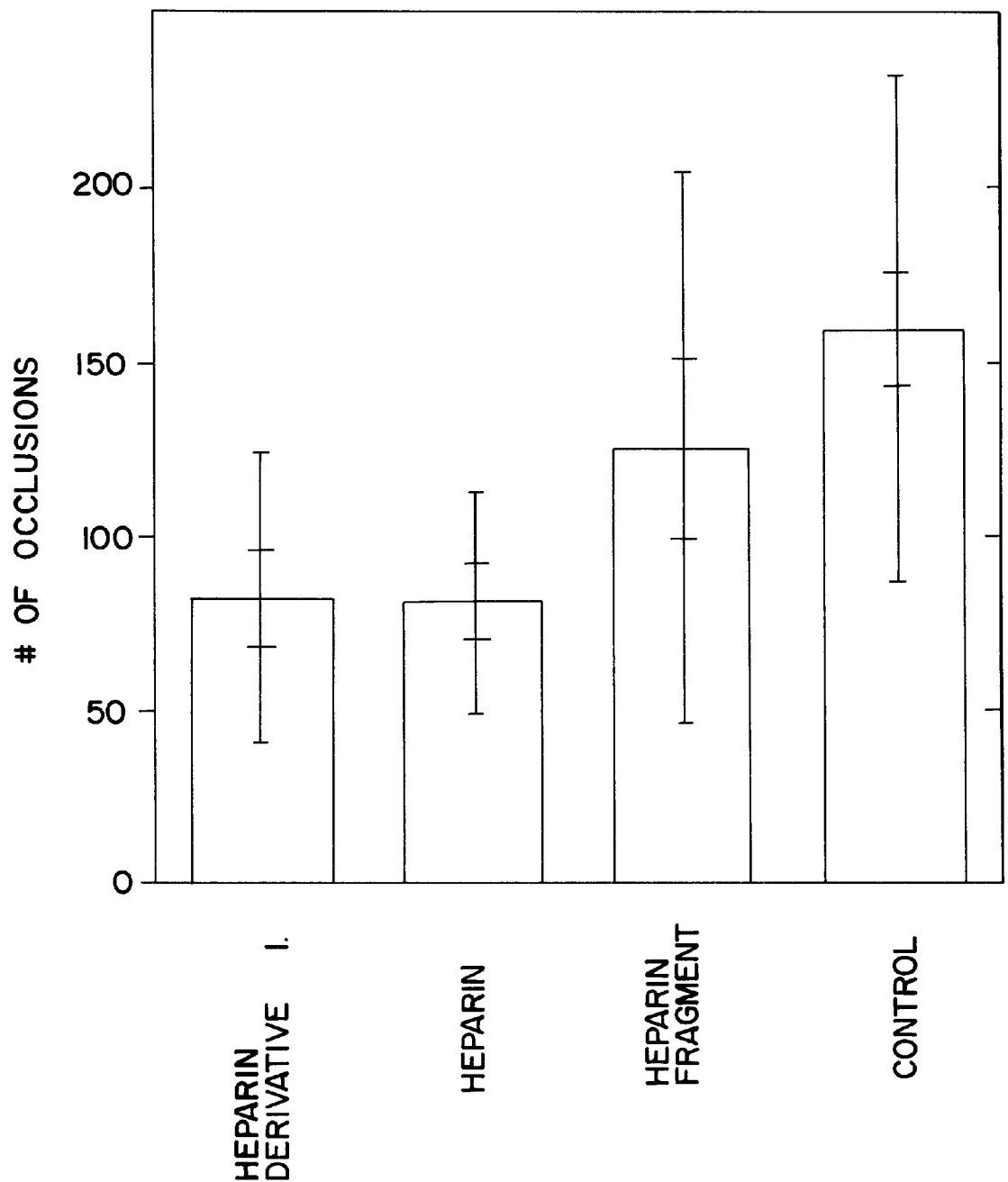

FIG. 6 The development of coronary collaterals by standard heparin, the heparin derivative 1 a low molecular weight heparin (heparin fragment) of molecular weight 4 800 and a control of no treatment. Only in the presence of heparin derivative 1 or heparin could the enhancement of coronary collateral development be shown as a statistically significant ($p<0,05$) decrease in the number of occlusions performed.

Figure 7:
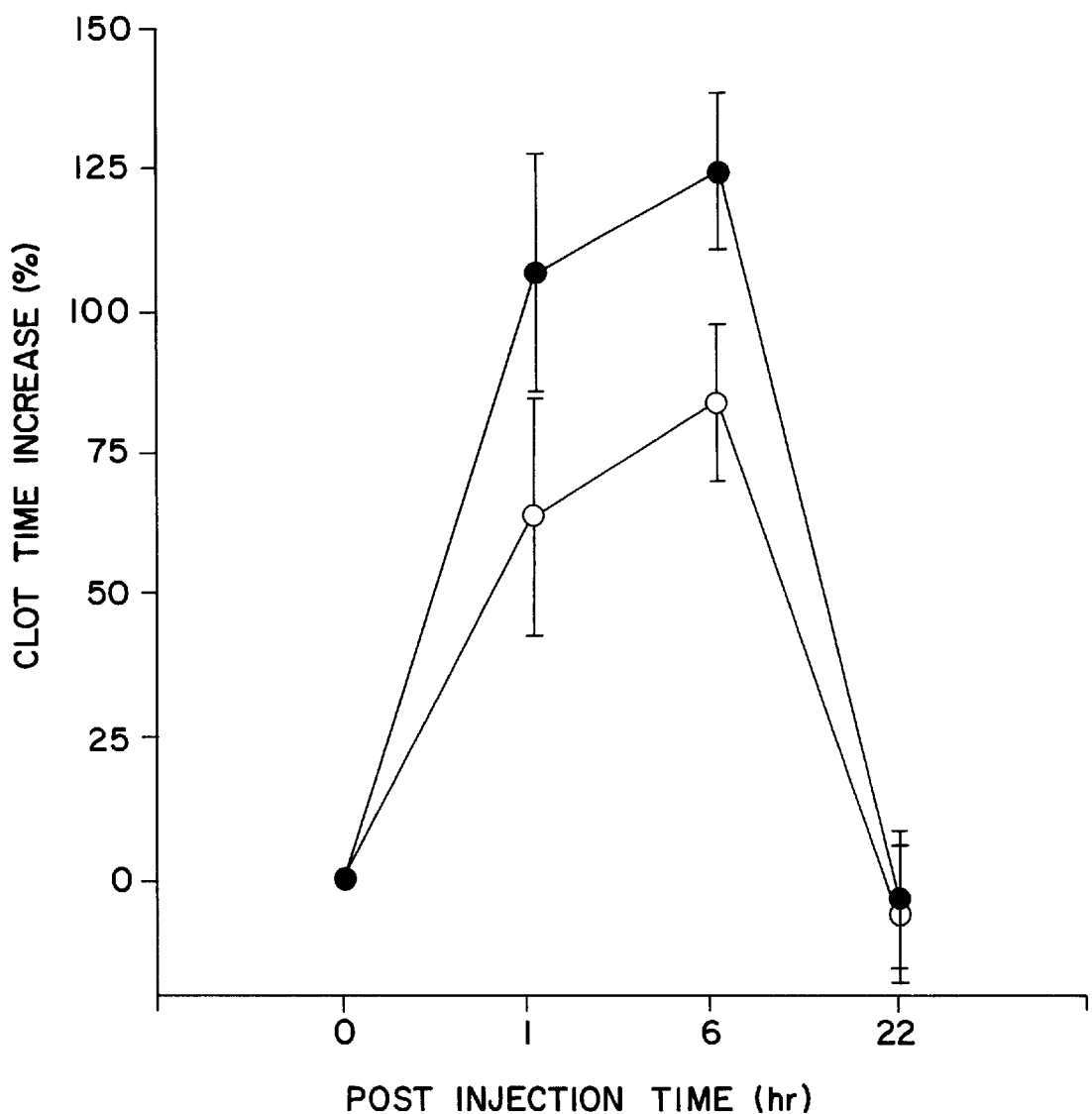

FIG. 7 The prolongation of the Lee-White clotting time (clot time increase %) iii the blood in dogs treated by subcutaneous injection with standard heparin (3.6 mg/kg) or heparin derivative 1 (10 mg/kg). Although the dose of heparin derivative 1 was three times larger (by weight) than for heparin the prolongation of the clotting time was less pronounced.

DESCRIPTION OF THE INVENTION

The invention relates to new heparin derivatives from bovine heparin which are characterised by:

having a molecular weight equal to or larger than the standard heparin.

showing a sulfur content which is equal to or higher than that of the starting heparin or at least 13% w/w.

having an anticoagulant activity in the anti-FXa assay of less than 10% of the standard heparin it was made from showing a ratio of APTT activity over anti-FXa activity of 3–35 showing a reduced prolongation of bleeding time compared to heparin as measured in the rat tail after i.v. administration and showing enhancement of the rate of development of coronary collaterals in dogs equal to or better than heparin.

The invention further relates to a process for preparation of new bovine heparin derivatives comprising the following steps:

oxidation by periodate at pH 4–5 at 0–10° C. in the dark partial depolymerization by alkali reduction by sodium borohydride and fractionating the obtained product by using gel permeation chromatography, ultrafiltration, hydrophobic interaction chromatography, affinity chromatography, ion exchange chromatography or precipitation from an aqueous solution by addition of an organic solvent preferably ethanol and collecting the product with a molecular weight not less than that of standard heparin used as starting material.

The purpose of the fractionation is to obtain a product of equal or higher molecular weight than standard heparin and also to obtained a more narrow molecular weight distribution than in the heparin or intermediate products.

The invention also relates to a process for preparation of new porcine heparin derivatives comprising a mild chemical sulfation oxidation by periodate at pH 4–5 at 0–10° C. in the dark partial depolymerization by alkali reduction by sodium borohydride fractionating the obtained product by using gel permeation chromatography, ultrafiltration, hydrophobic interaction chromatography, affinity chromatography, ion exchange chromatography or precipitation from an aqueous solution by addition of an organic solvent preferably ethanol and collecting the product with a molecular weight not less than that of the heparin used as starting material.

The invention thus relates to a process in which the novel heparin derivatives of the invention also are obtained when porcine heparin is used as starting material. For porcine heparin a mild sulfation is carried out prior to the oxidation by periodate and subsequent depolymerization. This mild sulfation enhances the total sulfate content of the porcine heparin and also blocks some of the vicinal hydroxyl groups of non-sulfated glucuronic acid and of iduronic acids which are susceptible to the oxidation by periodate. This sulfation will thus also lead to a lesser degree of depolymerization of the porcine heparin than described in EP 287 477.

The use of the product for the manufacture of a medicament for treatment of ischemic heart disease and related vascular disorders and for the enhancement of the rate of development of coronary collateral perfusion is also claimed. The method for treatment of ischemic heart disease and related vascular disorders and enhancement of the rate of development of coronary collaterals by administration of the product in a therapeutic dose are also parts of the invention.

One aspect of the invention is the molecular weight of the novel heparin derivatives of the invention. As will be shown in FIG. 6 a low molecular weight heparin (heparin fragment) of molecular weight 4 800 did not show the same good effect as the standard heparin at the same dose. FIG. 6 shows the importance of the molecular weight of the novel heparin for the enhancement of coronary collateral development. A further aspect of the invention is that the anti-FXa activity of the novel heparins is reduced to less than 10% of the activity of the standard heparin which is used as starting material for the preparation of the novel heparins of the invention. This is shown in Table 1. The anti-FXa activity commonly found in standard heparins of injectable grade is 120–190 IU/mg. The reduction in anti-FXa activity is caused by the oxidative treatment by periodate, alkali treatment and reduction. This treatment also influences the molecular weight of the final product.

Thus when periodate oxidation takes place at pH 3 the anti-FXa activity of the product was relatively high, 20–40%, of the original activity remained. This has also been shown in EP 14 184-B. However, when a pH of 7 was used, a low molecular weight heparin (heparin fragment) of molecular weight 4 800 was obtained. Thus a pH of 4–5 and preferable below 4.5 was used for the periodate step in the preparation of the novel heparin derivative of the invention.

In an Activated Partial Thromboplastin Time (APTT) anticoagulant assay the activity of the novel heparin derivatives of the invention is always higher than the activity in the anti-FXa assay. The ratio APTT over anti-FXa being 3–35 compared to a ratio of 0.8–1.2 in standard heparins and 0.5–0.05 for many low molecular weight heparins.

The levels of anticoagulant activity in vivo in dogs which was found in the novel heparin derivatives represent levels normally found when heparin is clinically used for thrombosis profylaxis in general surgery (this can be seen in FIGS. 3 and 4). The novel heparin derivatives of the invention therefore also have an antithrombotic potential while still having less of the unwanted bleeding side effect characteristic for standard heparin. The antithrombic activity was demonstrated in vivo in rabbits. (Table 2)

A further aspect of the novel heparins is the reduction in prolongation of the bleeding time (this can be seen from Table 1) which is very important because it allows the new products of the invention to be administered at higher and more effective doses than standard heparin without any risk of bleeding. By reduced prolongation of bleeding time is here meant a reduction of at least 75%.

Another aspect of the invention is the high sulfate content of the novel heparins which is equal to or preferable above that of the heparins used for starting material. This high sulfate content of the novel heparins is obtained by using as starting material a heparin which is rich in sulfate groups for example heparin from bovine lung reducing the anticoagulant activity of the starting heparin by using a procedure such as the periodate procedure described that eliminates nonsulfated uronic acids moieties of heparin thus increasing the proportion of sulfated uronic acid in the novel heparin derivatives employing a fractionation procedure that enriches the novel heparin derivatives with respect to highly sulfated components. Such a fractionation procedure could be precipitating the product from an aqueous solution of a sodium, calcium, zinc or barium salt by a water miscible solvent and in the case of calcium, zinc and barium salts, after the fractionation converting these salts to sodium salts or by a chromatographic procedure involving hydrophobic interaction, cation exchange or affinity chromatography. This fractionation procedure can be performed either before or after periodate procedure described or both techniques could be used together. An example of an affinity chromatography ligand is thrombin which could be coupled to Sepharose®.

In addition to these procedures for enhancing the sulfate content of the novel heparin derivatives of the invention chemically sulfation may optionally be used in order to enhance the sulfate content even further.

Methods for chemical sulfation of the products of the invention should be mild enough not to cause depolymerization or degradation of the product being sulfated. For example the products could be sulfated by treating their tributylammonium salts dissolved in dry dimethylformide at low temperature with a complex of sulfur trioxide and an organic base such as pyridine or triethylamine and then isolating and purifying the sulfated product using any one of the methods employed for fractionation in the periodate procedure. Since chemical sulfation of heparin as such generally decreases the anticoagulant activity of heparin as measured by the anti-FXa assay a milder periodate procedure may be used when combined with chemical sulfation compared to when the periodate procedure is used alone. In a different execution of the invention the preparation may begin with a mild partial chemical sulfation followed by a periodate procedure, which is a process preferred for porcine heparin.

The present invention thus relates to novel heparin derivatives for treatment of ischemic heart disease and related vascular disorders. These heparin derivatives can be administered at high doses for efficiently enhancing coronary collateral formation, inhibiting smooth muscle cell proliferation and they can also at the same time provide a sustained low level of anticoagulant activity in plasma which contributes to an antithrombotic effect without risk for hemorrhage. In clinical practice only a once daily subcutaneous injection needs to be administered instead of 2–3 subcutaneous or intravenous injections daily as is generally the case for standard heparin for example in clinical antithrombotic therapy. The dose of the novel heparin derivatives could be in the range of 0.5–15 mg/kg /day by subcutaneous injection or from a depot preparation. Intravenous infusion or injection could also be used.

Below are some non limiting examples for the production of the novel heparin derivatives.

EXAMPLES

Example 1

Heparin Derivative 1.

Standard bovine lung heparin (100 g), Mw=10,000, was dissolved in sodium acetate buffer (2.5 l) (0.05 M sodium acetate, 0.2 M sodium chloride, pH 5.0) and cooled to 4° C. Sodium periodate (107 g, 0.50 mol) dissolved in the sodium acetate buffer (2.5 l) was added and the mixture was stirred for 2 days. Ethylene glycol (100 ml) was added to destroy excess periodate and the mixture was left at room temperature for a few hours. The solution was desalted on a Sephadex G-15 column. The fraction containing the desalted product was freeze dried affording 81 g periodate oxidized heparin.

The periodate oxidized heparin was dissolved in 0.02 M sodium hydroxide (4.25 l) and was left at room temperature for 40 minutes and then reduced by sodium borohydride (4.25 g) for 2.5 hours. Excess sodium borohydride was decomposed by acetic acid (28 ml). This solution was then fractionated by ion exchange chromatography on a DEAE-Sepharose column. A fraction which eluted between 0.7 M and 2 M sodium chloride was collected and desalted using a hollow fiber (Amicon H1P3-20, cutoff 3000). The heparin derivative was precipitated by addition of cold ethanol (2,5 times the weight of the retentate). The precipitate was collected and dried in vacuum yielding 31 g of heparin derivative 1.

By elemental analysis N was 2.1% and S was 13.5%. By conductimetric titration the molar ratio $SO_3/CO_2$ was 2.82. By gel permeation chromatography the molecular weight was 11000 Da. For the heparin used as starting material in this example S was 13.0%, the molar ratio $SO_3/CO_2$ was 2.47 and the molecular weight by gel permeation chromatography was 10000 Da. The anti-FXa activity was 8 IU/mg, APTT 54 IU/mg and antithrombotic activity 4 IU/mg compared to 126 IU/mg, 151 IU/mg and 124 IU/mg, respectively, for the starting standard heparin. The heparin/cofactor II dependant antithrombotic activity (Tollefsen, D M et al. Blood (1985) 66, 769–774) was studied and found to be increased twofold compared to the starting standard heparin as well as compared to the intermediate periodate oxidized heparin and even more compared to the periodate oxidized, depolymerized and reduced heparin.

Example 2

Bovine lung heparin (100 g) was oxidized as for Example 1, ethylene glycol was added and the solution was desalted using a hollow fiber (Amicon H1P3-20 cutoff 3000). Freeze drying afforded 78 g oxidized heparin. This material (4.0 g) was dissolved in 0.1 M sodium hydroxide (200 ml) and left at room temperature for 2 hours and then reduced by sodium borohydride (0.18 g) over 3 hours. Excess of borohydride was decomposed by acetic acid (5 ml). The pH of the solution was then adjusted to 6.3 by sodium hydroxide (2 M). The solution was desalted by ultrafiltration. Freeze-drying afforded 3.7 g of an periodate oxidized, depolymerized and reduced product. In order to fractionate this product it was subjected to gel permeation chromatography on a Sephadex G-75 column, 2.00 g was dissolved in 0.2 M sodium chloride and was then passed through the column (5×83 cm) at a rate of 0.65 ml/min. A high molecular weight fraction was collected and desalted by ultrafiltration. Freeze-drying afforded 0.34 g of a novel heparin derivative. By elemental analysis S was 14.3% and anti-FXa was 7 IU/mg and APTT 55 IU/mg.

Example 3

Bovine lung heparin (2.0 g) was dissolved in sodium acetate buffer (50 ml) (0.05 M sodium acetate, 0.2 M sodium chloride, pH 4.0) and cooled to 4° C. Sodium periodate (2.14 g, 10 mmol) dissolved in the sodium acetate buffer (50 ml) was added and the solution was left at 7° C. for 3 days. Ethylene glycol (2 ml) was added to destroy excess periodate and the solution was left at room temperature for an hour, desalted by ultrafiltration (Amicon YM2). The retentate was neutralized to pH 6.5 and freeze-dried yielding 1.78 g periodate oxidized heparin. The periodate oxidized heparin (1.60 g) was dissolved in 0.1 M sodium hydroxide (80 ml) and was left at room temperature for 2 hours and then reduced by sodium borohydride (80 mg) for 3 hours. Excess sodium borohydride was decomposed by acetic acid (2 ml), neutralized to pH 6.5 and fractionated by ultrafiltration using a membrane with cutoff 8000 Da. The high molecular weight fraction retained on the ultrafilter was freeze dried. By elemental analysis S was 13.6% and anti-FXa was 5 IU/mg and APTT 26 IU/mg Example 4

Heparin derivative 2

Heparin derivative 1 (1.00 g, S=13.5%) was dissolved in water (20 ml) and passed through a cation exchange resin (Amberlite IR-120 in hydrogen form) (2×20 cm) and eluted with water (80 ml). The eluate was neutralized with tri-n-butylamine-ethanol 1:9 (11 ml) to pH 5,8 and extracted with diethyl ether (2×60 ml). The aqueous phase was freeze-dried and then dried in vacuum. The dried product was dissolved in dry N,N-dimethyl formamide (15 ml) and sulfur trioxide triethylamine complex (3.0 g) was added. The solution was kept at room temperature for 3 days and then poured into 3% sodium acetate dissolved in ethanol (150 ml). The mixture was centrifuged and the precipitate washed with ethanol (2×20 ml), dissolved in 2 M sodium chloride and ultrafiltrated (Amicon YM2, cutoff 1000). The retentate was washed with water and then passed through a cation-exchange resin (Amberlite IR-120, hydrogen form) and eluted with water. The eluate was neutralized with 0.1 M sodium hydroxide to pH 6.2 and freeze-dried yield 0.88 g. The elemental analysis showed a content of S of 15.7%. The molar ratio $SO_2/CO_2$ by conductimetric titration according to Casu, B and Gennaro H, (1975) Carbohydr. Res 39 168–176 was 3.92. The molecular weight by gel permeation chromatography was 11000 Da. The anti-FXa was 3 IU/mg and the APTT activity was 102 IU/mg.

Example 5

Porcine mucosa heparin(5.0 g) (11.3% S) was dissolved in water (75 ml) and passed through a cation exchange resin (Dowex 50WX8 in hydrogen form) (2.5×24 cm) and eluted with water (150 ml). The eluate was neutralized with tri-n-butylamine-ethanol (1:9) (50 ml) to pH 5.5 and extracted with diethyl ether (2×150 ml). The aq. phase was freeze-dried to yield 7.56 g product. The tributylammonium salt (0.50 g) was dried in vacuum and dissolved in dry N,N-dimethylformamide (5 ml) and sulfur trioxide triethylamine complex (0.15 g) was added. The solution was kept at room temperature for 18 hours and then poured into 3% sodium acetate in ethanol (45 ml). The mixture was centrifuged and the precipitate washed with ethanol (2×30 ml), dissolved in 2 M sodium chloride and ultrafiltrated (Amicon YM1, cutoff 1000). The retentate was washed with water and freeze-dried, yield 0.32 g.

The sulfated heparin (0.20 g) was dissolved in sodium acetate buffer (5 ml) (0.05 M sodium acetate, 0.2 M sodium chloride, pH 5.0). Sodium periodate (214 mg, 1 mmol) dissolved in the sodium acetate buffer (5 ml) was added and kept at +8° C. for one day. Ethylene glycol (0.5 ml) was added and the mixture was left at room temperature for a few hours, then the solution was desalted by ultrafiltration. The periodate oxidized heparin was dissolved in 0.1 M sodium hydroxide and left at room temperature for 2 hours and then reduced by sodium borohydride (14 mg). Excess sodium borohydride was decomposed by acetic acid (0.2 ml). This solution was fractionated by ion exchange chromatography on a DEAE-Sepharose column. A fraction which eluted between 0.7 M and 2 M sodium chloride was collected and further fractionated by ultrafiltration using a membrane with cutoff 10000 Da (Amicon YM10). The retentate was freeze-dried, yield 100 mg. By elemental analysis S was 13.8%.

Chemical and Bioloaical Tests

Molecular Weight Distribution.

FIG. 1 shows the molecular weight distribution on gel permeation chromatography by HPLC. (according to Sudhalter J et al, (1989) J. Biol. Chem, 264, 6892–6897) after chemical treatment and fractionation of heparin produced from bovine lung according to the claimed process.

When clinically used heparin produced from bovine lung (curve 1 in FIG. 1) was oxidized with periodate at pH 4–5 a distribution according to curve 2 in FIG. 1 was obtained. After treatment by strong base to effect depolymerization followed by reduction by sodium borohydride a product was obtained which unexpectedly showed a very minor shift in the molecular weight distribution (curve 3 in FIG. 1) compared to the starting bovine lung heparin (curve 1 in FIG. 1 ). In contrast to that, a product obtained from porcine heparin according to the same procedure showed a considerable shift in molecular weight distribution, compare curve 5 with curve 3 in FIG. 2. The shift to lower molecular weight seen in curve 5 was similar to the decrease in molecular weight distribution shown in EPO 287 477 which describes low molecular weight heparin.

FIG. 3 shows the molecular weight distribution on gel permeation chromatography by HPLC. (according to Sudhalter J et al, (1989) J. Biol. Chem, 264, 6892–6897) after chemical treatment and fractionation of heparin produced from porcine intestinal mucosa according to the claimed process for porcine heparin. When clinically used heparin produced from porcine intestinal mucosa (curve 6 in FIG. 3) sulfated, periodate oxidized, depolymerized by sodium hydroxide and reduced by sodium borohydride a distribution according to curve 7 in FIG. 3 was obtained. After treatment by strong base to effect depolymerization followed by reduction by sodium borohydride a product was obtained which unexpectedly showed a very minor shift in the molecular weight distribution (curve 8 in FIG. 3) compared to the starting heparin produced from porcine intestinal mucosa (curve 6 in FIG. 3).

This clearly shows that different products unexpectedly were obtained when clinical heparins from different species are used as starting material for the same procedure of periodate oxidation and alkaline depolymerization.

The product shown in curve 3 in FIG. 1 was further subjected to fractionation according to example 1 to give a new product of molecular weight distribution shown in curve 4 in FIG. 1 Other methods of fractionation to give the novel heparins of the invention are described in examples 2 and 3.

Determination of the Anti-factor IIa Potentiating Activity.

The anti-factor IIa potentiating activity of the new heparin derivatives was determined in a system in which it forms a complex with antithrombin. The antithrombin-heparin derivative mixture was incubated at 37° C. with factor II for 1 minute. An amount of factor IIa is neutralized by the antithrombin-heparin derivative complex in proportion to the concentration of the heparin derivative. The remaining factor IIa-activity was measured using the chromogenic substrate S-2238 (H-D-Phe-Pip-Arg-pNA). The rate of pNA formed was compared to the rate of pNA formed using the 4th International standard for heparin.

Testing of Anticoagulant Activity in Animal

The novel heparin derivatives were administered at 10 mg/kg to two Beagle dogs. Solutions (0.2 ml/kg) in saline were made and injected subcutaneously in the neck of the dog. Blood samples of 5 ml were collected using Venoject® containing 0.5 ml of 0.13 M sodium citrate. Four blood samples were drawn during the first hour of the experiment followed by one sample every hour up to 9 hours. The blood samples were kept at room temperature for 10 minutes, centrifuged for the separation of the plasma, which was immediately taken for the APTT analysis. Remaining plasma was kept frozen at −20° C. until analysis of anti-FXa activity. The anti-FXa was performed according to Bergkvist D., Hedner U., Sjödin E. and Holmer E. (1983) Thromb. Res. 32 381–391. The APTT assay was performed according to Teien, A. N. and Lie, M. (1975) Thromb. Res. 7 777–778. The results for heparin derivative 1 in the anti-FXa and APTT assays are seen in FIGS. 4 and 5 respectively. Anti-FXa activity could be measured in the blood plasma of the dog from about one hour after injection. This activity did not show any decrease after 9 hours which is shown in FIG. 4. Also a prolongation of the APTT activity was still present after 9 hours (see FIG. 5).

The levels of anticoagulant activity seen in FIG. 4 and FIG. 5 represent levels normally found when heparin is clinically used for thrombosis profylaxis in general surgery. The novel heparin derivatives of the invention therefore also have an antithrombotic potential while still having less of the unwanted bleeding side effect characteristic for standard heparin.

In the Activated Partial Thromboplastin Time (APTT) anticoagulant assay the activity of the novel heparin derivatives of the invention is always higher than the activity in the anti-FXa assay. The ratio APTT over anti-FXa being 3–35 compared to a ratio of 0.8–1.2 in standard heparins and 0.5–0.05 for many low molecular weight heparins.

The plasma concentration curves for the anticoagulant activities (FIGS. 4 and 5) are also advantageous over standard heparin in showing a consistent level of anticoagulant activity for a long time period (at least 9 hours). This means that in clinical practice only a once daily subcutaneous injection needs to be administered instead of 2–3 subcutaneous or intravenous injections daily as is generally the case for standard heparin for example in clinical antithrombotic therapy.

Bleeding Time Test.

A template bleeding time test according to Dejana E, Callioni A, Quintana A, Gaetano G, 1979 Thromb. Res 15 191–197 was performed in Sprague-Dawley rats weighing 200–250 g anaesthetized with Mebumal/Stesolid (Dumex A/S Copenhagen). The template device (Simplate, General Diagnostics, Durham, N.C.) was applied longitudinally to the dorsal part of the tail, taking care to avoid large veins. Blood from the wound was then carefully removed every 30 sec, with blotting paper. A minimum of six rats were used for each compound and dose. Bleeding times were measured from the moment the tail was incised until the first arrest of bleeding. The bleeding time was recorded with an accuracy of 30 sec. Two bleeding times were always determined in each rat, viz. 10 min before and 10 min after drug administration, and the results are expressed as the prolongation of bleeding time. (See Table 1)

TABLE 1

Bleeding time of heparins in the rat

| Compound | Anti-FXa# IU/mg | APTT# IU/mg | Dose mg/kg | Prolongation of bleeding time min## |
|---|---|---|---|---|
| Standard heparin | 126 | 151 | 2 | 12.8 |
| Heparin derivative 1 | 8 | 54 | 2 | 0.7 |
| | | | 4 | 1.6 |
| | | | 8 | 1.9 |
| Heparin derivative 2 | 3 | 102 | 2 | 0.5 |
| | | | 4 | 1.4 |

The anticoagulant assays used are describes under Testing of anticoagulant activity in animal.
The bleeding time (min) is expressed as the difference in bleeding time 10 min after and 10 min before drug administration.

This reduction in bleeding time of the novel heparin derivatives is very important because it allows the new products of the invention to be administered at higher and more effective doses than standard heparin without any risk of bleeding.

Testino of Antithrombotic Effect in Animal

The in vivo antithrombotic effect of Heparin derivative 1 was tested in a Wessler rabbit thrombus model (Wessler et al., J Appl Physiol 14,1959, 943–946). The rabbits were premedicated with atropine and Hypnorm® and anaesthetized with pentobarbitone. Part of each jugular veins was freed from surrounding tissue and the tributaries ligated. The test compound was injected intravenously (time 0) at doses 1 and 3.5 mg/kg. Fifteen minutes after drug administration the rabbit's coagulation system was activated by means of an intravenous injection of glass activated human plasma. Exactly 30 seconds after this thrombotic challenge, a two cm long segment of the right jugular vein was sealed off for ten minutes in order to achieve stagnant blood. The segment was then cut out and its content was poured into a Petri dish and visually examined and the thrombus, if any, was scored according to a system described below. After another 15 minutes (30 minutes after injection of the test compound) the rabbit received a new thrombotic challenge and the left jugular vein was sealed off and examined as described above. This procedure allows us to study the antithrombotic effect of Heparin derivative 1 at two occasions (15 and 30 minutes after dosing) and thus, it is possible to estimate the duration of the antithrombotic effect. Heparin derivative 1 was evaluated at 2 doses with at least 6 rabbits in each dose group. The antithrombotic activity of the test compound is evaluated according to a scoring system defined as follows:

| Score | Composition of vessel content |
|---|---|
| 0 | represents blood without ant visible fibrin strands in the sealed vessel segment |
| 1 | is equal to small, hardly visible fibrin strands |
| 2 | is equal to several very small fibrin clots |
| 3 | is equal to one or two bigger clots |
| 4 | reperesents the formulation of a big thrombus forming a cast of the isolated vessel |

The antithrombotic activity of Heparin derivative 1 is described by an "antithrombogenic index" ranging from 0 (highly antithrombotic) to 1 (non antithrombotic). This index is obtained by dividing the sum of the thrombotic scores in each dose group with 4×n which is the score that is obtained with a non antithrombotic reference compound (physiological NaCl). The antithrombotic activity of Heparinderivative 1, specific anti-FXa activity 8 IU/mg, was tested at 3.5 and 1 mg/kg using at least 6 rabbits in each dose group. The results, expressed as antithrombotic score for each individual rabbit as well as antithrombotic index for groups of rabbits received the same dose are summarized in Table 2.

TABLE 2

ANTITHROMBOTIC ACTIVITY IN RABBITS
Heparin derivative 1

| DOSE | ANTITHROMBOTIC SCORE | | ANTI-THROMBOTIC INDEX | |
|---|---|---|---|---|
| | 15 min | 30 min | 15 min | 30 min |
| 3.5 mg/kg | 0, 0, 0, 0, 0, 0, | 0, 0, 0, 0, 0, 0, | 0.00 | 0.00 |
| 1 mg/kg | 3, 2, 3, 1, 3, 1, 2, 1 | 4, 4, 4, 4, 2, 1, | 0.47 | 0.79 |
| Saline | 4, 4, 4, 4 | 4, 4, 4, 4 | 1.00 | 1.00 |

This experiment very clearly shows the antithrombotic activity of the claimed novel heparin derivative in a dose in which the bleeding time is not prolonged (table 1)

Antiproliferative Effect on Smooth Muscle Cell

The novel heparins of the invention showed an antiproliferative effect on the growth of arterial smooth muscle cells from rats grown in cell culture. An inhibition of 50% of the cell proliferation was obtained by a concentration of 50 $\mu$g/ml in the cell culture medium. This is the same concentration which is needed when clinically used standard heparin was used.

Enhancement of the Coronary Collateral Development

The enhancement of the coronary collateral development by the novel heparins of the invention was examined according to the procedure described by Fujita et. al. (1987) Japanese Circulation Journal 51 395–402. In this work it is demonstrated that in the presence of severe myocardial ischemia which is known to promote collateralization, heparin accelerated the development of coronary collaterals. The dosis of heparin in the experiment of this publication was determined by its ability to maintain an anticoagulant activity in the plasma of the dogs which was measured as a doubled Lee-White clotting time. The effect of standard heparin, the heparin derivative 1, a low molecular weight heparin (heparin fragment of molecular weight of 4 800 and a control of no treatment on the enhancement of coronary collaterals is shown in FIG. 6. Only in the presence of heparin derivative 1, or heparin could the enhancement of coronary collateral development be shown as a statistically significant (p <0.05) decrease in the number of occlusions needed. When the novel heparin derivative 1 of the invention was administered once daily by subcutaneous administration at a dose of 10 mg/kg bodyweight the same degree of enhancement of coronary collateral development was found as was seen by the standard heparin dose used by Fujita et al (1987) (see FIG. 6)

Prolongation of the Lee-White Clotting Time.

A statistically significant decrease in the prolongation of the Lee-White clotting time was observed for the new heparin derivative compared to the heparin concentration used before, see FIG. 7. (Lee-White clotting time test is described in Clinical Interpretation of Laboratory Test. Ed. Godal (1950) page 30).

The prolongation of the Lee-White clotting time (clot time increase %) in the blood in dogs treated by subcutaneous injection with standard heparin (3.6 mg/kg) or heparin derivative 1 (10 mg/kg). The dose of heparin derivative 1 was three times larger (by weight) than for heparin but the prolongation of the clotting time was nevertheless smaller.

What is claimed is:

1. Process for preparation of bovine heparin derivatives comprising:
    a) oxidizing bovine heparin using periodate at pH 4–5 at 0–10° C. in the dark,
    b) partially depolymerizing the product from step a) using alkali,
    c) reducing the product from step b with sodium borohydride,
    d) fractionating the obtained product by using gel permeation chromatography, ultrafiltration, hydrophobic interaction chromatography, affinity chromatography, ion exchange chromatography or precipitation from an aqueous solution by addition of an organic solvent,
    e) collecting the product with a molecular weight not less than that of the bovine heparin used as starting material.

2. The process of claim 1 wherein said organic solvent is ethanol.

3. Heparin derivatives from bovine heparin obtained by the process of claim 1 and characterized by:
    having a molecular weight equal to or larger than standard bovine heparin,
    showing a sulfur content which is equal to or higher than that of said bovine heparin or at least 13% w/w,
    having an anticoagulant activity in the anti-FXa assay of less than 10% of said bovine heparin it was made from,
    showing a ratio to APTT activity over anti-FXa activity of 3–35,
    showing a reduced prolongation of bleeding time compared to said bovine heparin it was made from as measured in the rat tail after i.v. administration, and
    showing enhancement of the rate of development of coronary collaterals in dogs equal to or better than clinically used heparin.

4. Process for preparation of porcine heparin derivatives comprising:
    a) subjecting porcine heparin to a mild chemical sulfation,
    b) oxidizing the product from step a) using periodate at pH 4–5 at 0–10° C. in the dark.
    c) partially depolymerizing the products from step b) using alkali,
    d) reducing the product from step c) with sodium borohydrine, e) fractionating the obtained product by using gel permeation chromatography, ultrafiltration, hydrophobic interaction chromatography, affinity chromatography, ion exchange chromatography or precipitation from an aqueous solution by addition of an organic solvent, f) collecting the product with a molecular weight not less than that of the porcine heparin used as starting material.

5. The process of claim 4 wherein said organic solvent is ethanol.

6. Heparin derivatives from porcine heparin obtained by the process of claim 4 and characterized by:

having a molecular weight equal to or larger than standard porcine heparin, showing a sulfur content which is equal to or higher than that of said porcine heparin or at least 13% w/w, having an anticoagulant activity in the anti-FXa assay of less than 10% of said porcine heparin it was made from, showing a ratio to APTT activity over anti-FXa activity of 3–35, showing a reduced prolongation of bleeding time compared to said porcine heparin it was made from as measured in the rat tail after i.v. administration, and showing enhancement of the rate of development of coronary collaterals in dogs equal to or better than clinically used heparin.

\* \* \* \* \*